United States Patent [19]
Littau et al.

[11] Patent Number: 6,054,616
[45] Date of Patent: Apr. 25, 2000

[54] PROCESS FOR REDUCING RESIDUAL RAW MATERIAL IMPURITIES IN TERTIARY AMINE OXIDES

[75] Inventors: Cheryl Ann Littau, Liederbach, Germany; Graham Cox, Huddersfield; Michael Neil Holland, Halifax, both of United Kingdom

[73] Assignee: Clariant Finance (BVI) Limited, Tortola, Virgin Islands (Br.)

[21] Appl. No.: 09/277,302

[22] Filed: Mar. 26, 1999

[51] Int. Cl.[7] ................................................. C07C 291/04
[52] U.S. Cl. ................................. 564/298; 564/2; 564/297
[58] Field of Search ................................. 564/2, 297, 298

[56] References Cited

U.S. PATENT DOCUMENTS

| | | | |
|---|---|---|---|
| 3,283,007 | 11/1966 | Chadwick | 260/583 |
| 3,432,555 | 3/1969 | Mahnken | 260/583 |
| 4,247,480 | 1/1981 | Murata et al. | 564/298 |
| 5,583,258 | 12/1996 | Hawkins | 564/298 |
| 5,710,333 | 1/1998 | Bader et al. | 564/298 |

*Primary Examiner*—Peter O'Sullivan
*Attorney, Agent, or Firm*—Miles B. Dearth

[57] ABSTRACT

The claimed process consists in treating the tertiary amine oxide with a sulphite or a bleach activator.

4 Claims, No Drawings

PROCESS FOR REDUCING RESIDUAL RAW MATERIAL IMPURITIES IN TERTIARY AMINE OXIDES

BACKGROUND OF THE INVENTION

The use of amine oxides as a detergent raw material is well established. Typical applications for this product group include foam boosters in liquid detergents, fragrance solubilisers and thickeners in various systems including thickened hypochlorite bleach cleaners. Alkyl-dimethylamine oxides, where the alkyl chain is generally of fatty origin and in the range of $C_8$–$C_{22}$, are commonly used for detergent applications.

The synthesis of the amine oxides involves the oxidation of a tertiary amine, which is usually accomplished by reaction of the amine with hydrogen peroxide.

An issue with this product group has been the presence of residual raw materials, specifically unreacted residual amine and hydrogen peroxide.

Hydrogen peroxide can be particularly problematic. For example, in thickened hypochlorite bleach formulations, this can lead to reaction with sodium hypochlorite and subsequent decomposition resulting in the evolution of oxygen. This can cause formulations to foam, resulting in processing and packing difficulties. The residual hydrogen peroxide may also react unfavorably with dyes and perfumes often used in household and cosmetic formulations.

Residual tertiary amine may also create difficulties for the formulator. This is particularly true with respect to viscosity characteristics of formulations, as well as potential problems with odour and colour. Other unwanted by products may form when these products containing high levels of residual amine are used in certain formulations. Reduction of the residual level of amine will reduce the formation of these products.

SUMMARY OF THE INVENTION

It is the object of this invention to reduce the presence of these residual raw material impurities in amine oxides, which will have the subsequent effect of reducing or eliminating the problems described.

According to the present invention there is provided a process for reducing residual raw material impurities in tertiary amine oxides which consists in treating the amine oxide with a sulphite or a bleach activator.

From 0.50 to 1.1 molar equivalents of sodium sulphite or of the bleach activator (preferably 0.9–1.0 molar equivalents) is added to the tertiary amine oxide reaction mixture after the product has been deemed to be as fully converted as practicable under normal reaction conditions (usually 98%+ based on tertiary amine charge). The sodium sulphite or bleach activator is added at a reaction mixture temperature of 25–95° C., preferably 65–95° C. The reaction is allowed to proceed for one hour, resulting in residual hydrogen peroxide levels of less than 0.005% as determined by sodium thiosulphate titration and less than 10 ppm as determined by Merck test strips (Merckoquant® peroxide test strips 1.10081.0001).

DESCRIPTION OF THE PREFERRED EMBODIMENTS

It is believed that the sulphite, in most cases sodium sulphite is converted to sodium sulphate while removing the residual $H_2O_2$ in the crude amide oxide. In the case of the bleach activator a per-acid is generated by reaction of the residual hydrogen peroxide with the bleach activator thus reducing the level of residual hydrogen peroxide. The per-acid in turn reacts with residual tertiary amine by converting it into tertiary amine oxide.

Suitable bleach activators are many reactive organic compounds having an O-acyl or N-acyl group. Representative examples such as N,N,N',N'-tetraacetylethylenediamine (TAED), glucose pentaacetate (GPA), xylose tetraacetate (TAX), sodium-4-benzoyloxybenzenesulfonate (SBOBS), sodium trimethylhexanoyloxybenzenesulfonate (STHOBS), N-nonanoylamido-hexanoyloxy-benzenesulfonic acid, tetraacetylglucoluril (TAGU), tetraacetylcyanic acid (TACA), isononanoyloxybenzenesulfonate, nonanoyloxybenzenesulfonate, amidocaproicacidphenolestersulfonate, di-N-acetyldimethylglyoxide (ADMG), 1-phenyl-3-acetylhydantoin (PAH), ammoniumnitriles are described in GB-A-836 988, GB-A-907 356, EP-A-0 098 129 and EP-A-0 120 591. Preferred bleach activator is TAED.

This process can be applied to all kinds of tertiary amine oxides, especially those of the formula $R^1$, $R^2$, $R^3 N \rightarrow O$ wherein $R^1$ is $C_8$–$C_{22}$-alkyl or $C_8$–$C_{22}$-alkenyl and $R^2$ and $R^3$ are $C_1$–$C_4$-alkyl, preferably $CH_3$.

Experimental:

Notes on analytical methods (i) Hydrogen Peroxide concentrations were determined using the well documented method of titration with Sodium thiosulphate (0.1M, 0.01 M) with potassium iodide as an indicator (back titration of liberated Iodine) or by using Merkoquant® peroxide test strips.

(ii) Amine Oxide and free fatty tertiary amine were determined using a well documented potentiometric titration with perchloric acid. (DIN ISO 2871)

1. Preparation of Alkyl Dimethylamine Oxide:

492.5 g of lauryldimethylamine, 997.4 g distilled water and 1.0 g ethylenediamine tetraacetic acid, sodium salt and 6.0 g of a polycarboxylic acid such as maleic or citric acid if required, were charged to a suitable reaction flask. The material was heated to 77° C. and 217.8 g of hydrogen peroxide (35%, aqua or an equivalent of any other concentration) were added slowly to control any exotherm. The reaction was monitored for amine oxide formation, and tertiary fatty amine and hydrogen peroxide reduction.

| Time (mins) | Free Peroxide* (%) | Free tertiary amine (%) | Amine oxide (%) |
|---|---|---|---|
| 30 | 0.2 | 0.98 | 29.89 |
| 180 | 0.14 | 0.65 | 30.21 |
| 300 | 0.09 | 0.45 | 30.51 |

*Determined via titration with sodium thiosulphate.

1. Reduction of Residual Hydrogen Peroxide Using Sodium Sulphite 500 g of Lauryldimethylamine oxide produced using the method indicated above was taken and charged to a suitable reaction flask. The temperature was raised to 65–95° C. Samples were then analyzed to determine free fatty amine content and free hydrogen peroxide content.

Free amine (%) 0.45
Free Peroxide (%) 0.09

At 65–95° C. 1.67 g of sodium sulphite, equimolar to the hydrogen peroxide level, was added. The amine oxide was then held at 65–95° C. for 1 hour and the residual hydrogen peroxide content monitored.

| Time (mins) | Free Peroxide (%) | Free tertiary amine (%) |
|---|---|---|
| 0 | 0.09 | 0.45 |
| 15 | 0.055 | 0.45 |
| 25 | 0.035 | 0.45 |
| 35 | 0.02 | 0.45 |
| 45 | 0.01 | 0.45 |
| 65 | 0.0048 | 0.45 |
| 65 | <10 ppm** | 0.45 |

**Merckoquant peroxide test strips No: 1.10081.0001

No subsequent decrease in fatty tertiary amine was observed. Amine oxide concentration remained constant (at ca. 30.51%).

2. Reduction of Residual Hydrogen Peroxide Using TAED.

a) 500 g of Lauryl dimethylamine oxide produced using the method indicated was taken and charged to a suitable reaction flask. The temperature was raised to 65–95° C. The reaction mixture was analyzed to determine free fatty amine content and free hydrogen peroxide content.

Free amine (%) 0.45
Free Peroxide (%) 0.09

The following calculation was used to determine the required amount of TAED:

0.09/100*500 g=0.45/34
=0.0132 moles $H_2O_2$
0.0132*1.1=0.01452 moles.

Molecular weight of TAED=228;

with 2 reactive sites so 228/2=114 effective molecular weight.

0.01452*114=1.655 g TAED (100%) required.

At 65–95° C. 1.66 g of TAED, ratio of 1.1:1 to hydrogen peroxide level was added. The amine oxide was then held at 65–95° C. for 1 hour and the residual hydrogen peroxide content monitored.

| Time (mins) | Free Peroxide (%) | Free tertiary amine (%) |
|---|---|---|
| 0 | 0.09 | 0.45 |
| 15 | 0.048 | |
| 25 | 0.030 | |
| 35 | 0.021 | |
| 45 | 0.01 | |
| 55 | 0.0037 | 0.20 |
| 55 | <10 ppm** | 0.20*** |

**Merckoquant peroxide test strips No: 1.10081.0001.
***Limit of detection.

Amine Oxide (%) 30.75

The amine oxide level was seen to increase whilst the free fatty tertiary amine level was reduced.

b) 680 g of amine oxide previously produced was charged to a suitable reaction flask and heated to 65–95° C. The product was analyzed as follows:

| | |
|---|---|
| Amine Oxide (%) | 29.93 |
| Free amine (%) | 0.54 |
| Free peroxide (%) | 0.073 |

1.66 g of TAED was added to the material based on a 1:1 ratio with hydrogen peroxide in 1 aliquots 10 minutes apart. The hydrogen peroxide and free amine level was monitored as shown:

| Time (mins) | Peroxide (%) | Free amine (%) | Amine Oxide (%) |
|---|---|---|---|
| 0 | 0.073 | 0.54 | 29.93 |
| 15 | 0.018 | 0.26 | |
| 30 | 0.01 | 0.21 | |
| 45 | 0.005 | 0.21 | 30.26 |
| 45 | <10 ppm** | | |

**Merckoquant peroxide test strips No: 1.10081.0001

It can be seen that hydrogen peroxide and free amine levels decrease whilst amine oxide increases as discussed previously.

What is claimed is:

1. A process for reducing residual raw material impurities in tertiary amine oxides which consists in treating the tertiary amine oxide with a bleach activator.

2. A process as claimed in claim 1 wherein tetraacetylethylene diamine are used.

3. A process as claimed in claim 1 wherein the bleach activator is used in an amount of 0.5 to 1.1 molar equivalent to the tertiary amine oxide.

4. A process as claimed in claim 1 wherein a tertiary amine oxide is used of the formula $R^1R^2R^3N \rightarrow O$ wherein $R^1$ is $C_8$–$C_{22}$-alkyl or $C_8$–$C_{22}$-alkenyl and $R^2$ and $R^3$ are $C_1$–$C_4$-alkyl, preferably methyl.

* * * * *